United States Patent
Alt

Patent Number: 6,099,561
Date of Patent: Aug. 8, 2000

[54] VASCULAR AND ENDOLUMINAL STENTS WITH IMPROVED COATINGS

[75] Inventor: Eckhard Alt, Ottobrunn, Germany

[73] Assignee: Inflow Dynamics, Inc., Wilmington, Del.

[21] Appl. No.: 09/175,919

[22] Filed: Oct. 20, 1998

Related U.S. Application Data

[63] Continuation-in-part of application No. 08/733,553, Oct. 20, 1996, Pat. No. 5,824,045, and a continuation-in-part of application No. 09/059,053, Apr. 11, 1998.

[51] Int. Cl.⁷ .................................................. A61F 2/06
[52] U.S. Cl. ..................... 623/1.44; 623/1.46; 623/1.39; 623/1.34
[58] Field of Search .................................... 606/191, 194, 606/195, 198; 623/1.34, 1.39, 1.42, 1.43, 1.44, 1.45, 1.46, 12

[56] References Cited

U.S. PATENT DOCUMENTS

| | | | |
|---|---|---|---|
| 4,101,984 | 7/1978 | MacGregor | 606/72 |
| 5,163,958 | 11/1992 | Pinchuk | 623/11 |
| 5,591,224 | 1/1997 | Schwartz et al. | 623/12 |
| 5,607,442 | 3/1997 | Fischell et al. | 606/191 |
| 5,607,463 | 3/1997 | Schwartz et al. | 623/1 |
| 5,824,077 | 10/1998 | Mayer et al. | 623/1 |
| 5,843,172 | 12/1998 | Yan | 606/191 |
| 5,858,556 | 1/1999 | Eckert et al. | 623/1 |

Primary Examiner—Michael Buiz
Assistant Examiner—David O. Reip

[57] ABSTRACT

A vascular or endoluminal stent is adapted for deployment in a vessel or tract of a patient to maintain an open lumen therein. The stent includes a biocompatible metal hollow tube constituting a base layer having a multiplicity of openings through an open-ended tubular wall thereof, the tube constituting a single member from which the entire stent is fabricated, and a thin, tightly adherent intermediate layer of noble metal overlying the entire exposed surface area of the tube including edges of the openings as well as exterior and interior surfaces and ends of the wall. A third, outermost ceramic-like layer composed of an oxide, hydroxide or nitrate of a noble metal is formed atop and in adherent relation to the intermediate layer.

41 Claims, 1 Drawing Sheet

VASCULAR AND ENDOLUMINAL STENTS WITH IMPROVED COATINGS

CROSS-REFERENCE TO RELATED APPLICATIONS

This application is a continuation-in-part of application Ser. No. 08/733,553, filed Oct. 20, 1996 now U.S. Pat. No. 5,824,045, issued Oct. 20, 1998 ("the '045 patent"), and of co-pending application Ser. No. 09/059,053, filed Apr. 11, 1998 ("the '053 application"), both of which are by the same inventor and assignee as the instant application.

BACKGROUND OF THE INVENTION

The present invention relates generally to stents which are implantable or deployable in a vessel or duct within the body of a patient to maintain the lumen of the duct or vessel open, and more particularly to improvements in stent coatings and in methods for applying such coatings.

Stents are expandable prostheses employed to maintain narrow vascular and endoluminal ducts or tracts of the human body open and unoccluded, such as a portion of the lumen of a coronary artery after dilatation of the artery by balloon angioplasty, for example. The stent itself has the basic form of an open-ended tubular element with openings through a side thereof, which is adapted to be expanded from a first outside diameter sufficiently small to allow the stent and its delivery system to traverse the vascular system of the human body to reach a site in the blood vessel at which the stent is to be deployed, to a second outside diameter sufficiently large to engage the inner lining of the vessel for retention at the site.

In the exemplary case of an occluded coronary artery, the original blockage typically arises from a buildup of fatty deposits or plaque on the inner lining of the vessel. The balloon angioplasty procedure is used to compress the deposits against the inner lining of the vessel, or virtually entire removal may be achieved using other types of angioplasty such as laser or rotational cutting. A different mechanism, however, may cause a new blockage after the angioplasty procedure is performed. The blood vessel wall is subjected to trauma by the balloon, laser or rotating knife, as the case may be, which results in intimal hyperplasia, i.e., a rapid proliferation of smooth muscle cells in the affected region of the wall, to cause restenosis and re-occlusion of the vessel lumen in a significant percentage of angioplasty patients within a period of from three to six months following the initial procedure.

To avoid this re-occlusion and to maintain the lumen of the vessel open, it is now customary procedure to install a stent at the site in the vessel where the angioplasty was performed. The stent is deployed by radial expansion under pressure exerted, for example, by active inflation of a balloon of a balloon catheter on which the stent is mounted, or in some instances by passive spring characteristics of a pre-formed elastic stent, to engage the inner lining or inwardly facing surface of the vessel wall with sufficient resilience to allow some contraction but also with sufficient stiffness to resist to a great degree the natural recoil of the vessel wall that follows its expansion.

The stent itself, however, offers a surface that can promote thrombus formation as blood flows through the vessel. This can result in an acute blockage, which, in a coronary artery, is sufficient to produce an infarction. The thrombosis and clotting can be reduced or even eliminated by localized application of appropriate drugs in a biodegradable formulation, which act for only a period of time sufficient to stave off the thrombus reaction to the presence of the stent in the bloodstream. Some difficulty is encountered in providing a stent surface which is suitable for retention of the necessary drug(s) to achieve those purposes.

A similar situation is encountered at the outward facing surface of the stent that contacts and engages the inner lining of the vessel, duct or tract, where tissue irritation can exacerbate fibrosis of the vessel wall and restenosis in the region of the irritation. Here, also, it would be desirable to provide the stent with the capability to provide a timed release of suitable drug(s) from a biodegradable carrier on or in the affected stent surface, to reduce the occurrence of fibrosis and hyperplasia at the portion(s) of the vessel wall contacted by the stent.

Another factor affecting the decision to implant a stent is the ability of the patient to tolerate the presence of the material of which the stent is composed. Here again, biomaterial coatings can be helpful. But a statistically significant five percent of the patient population is allergic to materials of which currently available stents are composed, including chrome, nickel, and/or medical grade implantable 316L stainless steel, which contains about 20% nickel. In such patients, stent implants are contraindicated and may be used only for acute relief on an emergency basis. Indeed, restenosis can commence within only one or two days to very quickly eliminate the initial benefit enjoyed from implantation of a conventional stent.

An additional need encountered for stent usage in the human body include a capability to clearly visualize the stent by means of X-ray fluoroscopy as it is being implanted at the preselected site in the body, as by advancement on a stent delivery system through a portion of the patient's vascular system and into a coronary artery, and after the stent is implanted, for purposes of its examination from time to time at the implant site. This generally requires that the wall of the stent be of sufficient thickness to not only withstand the aforementioned vessel wall recoil phenomenon, but to enable it to be seen on the fluoroscope.

Several materials possess the mechanical strength which is suitable for use in a stent structure, one which is particularly effective being 316L stainless steel. Typical stent wall or wire thicknesses range from 70 to 200 microns (or micrometers, em). A 70 to 80 $\mu$m thick 316L steel stent, clearly at the lower end of this range, has been found to provide sufficient strength to resist recoil and to maintain a lumen diameter very nearly corresponding to that achieved by the balloon inflation. But this relatively thin and tiny metal structure creates little shadow on a fluoroscopic picture, since the X-ray absorption of the metal is low. On the other hand, a need for greater wall thickness to enhance radiopacity must be balanced against an increased stent diameter which makes passage through narrow vessels more difficult and risky, as well against a requirement of sufficient radial force to be applied by balloon inflation on the interior surface of the stent during deployment, with concomitant increased risk of balloon rupture.

Among the most important features of a suitable stent are the following. The device should be flexible, and yet possess sufficient mechanical strength to resist vessel recoil. It should demonstrate a high rate of successful interventional placement, be highly visible on x-ray fluoroscopy, be very thin to minimize obstruction by its mere presence in the lumen intended to be dilated and held open, and not be an agent which promotes a re-narrowing or re-occlusion of the vessel or duct lumen in which it is implanted. Stent design, of course, can play a major role in influencing the aforementioned features, but also significant is the material(s) of which the stent is composed, with respect to visibility, flexibility, and recoil-resistant characteristics of the stent, as well as its surface characteristics that affect capability of the stent to prevent or inhibit thrombus formation and restenosis in a blood vessel in which the stent is implanted. Current stents have not proved to be capable of fulfilling all of these requirements.

Aside from vascular usage, other ducts or tracts of the human body in which a stent might be installed to maintain an open lumen include the tracheo-bronchial system, the biliary hepatic system, the esophageal bowel system, and the urinary tract system. Many of the same requirements are found in these other endoluminal usages.

Therefore, among the principal aims of the present invention are to provide a stent which has a composition that offers an enhanced capability to fulfill these important requirements, as well as which enables optimum mechanical support of the vessel despite a thin stent diameter and low profile while still offering optimum fluoroscopic appearance so that the position of the stent within the vascular system is readily identified.

Another aim of the invention is to provide such a stent which possesses farther properties and characteristics to deter restenosis even without biomaterial coatings, as well as avoid allergic reaction of the patient to the presence of the implanted stent.

SUMMARY OF THE INVENTION

Despite improvements in the design and construction of coronary stents, clinical practice has shown that restenosis remains a problem of major concern. One of the factors that contribute to restenosis pertains to the ability of the body to incorporate the implanted foreign material quickly. Both basic research with cell cultures and animal experiments have demonstrated that the degree of endothelialization of the foreign body determines the amount of the restenosis. Although the current assumption among industry practitioners and researchers is that a highly polished and smooth surface is beneficial to prevent stent thrombosis and to facilitate endothelialization, experiments conducted by the applicant herein have indicated that this is only partially true.

A significant reason for the lack of a high clinical success rate with electropolished stents is the fact that the smooth muscle cells which seek to envelop a foreign body such as a stent strut into the vessel wall require a higher degree of proliferation to cover this foreign body. The continuing flow of blood with a high pressure and high shearing stress prevents the migration of smooth muscle cells, which proliferate from the media and adventitial cells of a stented vessel such as a coronary artery in the body.

It has been shown that a slightly rough surface considerably facilitates the coverage by smooth muscle cells, leading to a functional endothelial layer even after 10 to 14 days. In addition to coverage by smooth muscle cells, an endothelial layer with a single layer of endothelial cells seals the neointima and thereby prevents the proliferation stimulus which facilitates and enhances the proliferation of cells over the mere coverage of the foreign body.

Another major finding is that the thinner the stent strut, the less the lumen of the stented vessel is obstructed. Moreover, a thin stent is more easily covered by a proliferative response such as a neoendothelial build-up. Accordingly, it is desirable to make stents with a wall as thin as can be practically achieved. As noted above, however, the visibility of stainless steel in a thickness below 50 $\mu$m is very poor, so that it becomes very difficult for the implanting physician to visualize the stent during the implantation procedure, and almost impossible to do so after the implantation has been performed, attributable to the limited extinction of x-rays by such a thin metal tube.

The aforementioned '045 patent is directed to an invention in which a vascular or endoluminal stent, such as one composed of medical grade implantable 316L stainless steel, is covered with a very thin, highly adherent layer of gold or other noble metal, such as platinum, or an alloy which is primarily gold or other noble metal, or even other metal having a high Z-number. Since gold has a 6× higher radiopacity than stainless steel, a 10 $\mu$m layer of gold provides fluoroscopic visualization equivalent to 60 $\mu$m thickness of stainless steel. Thus, a gold coating, for example, offers a substantially radiopaque surface that enables the stent to be observed without any difficulty as it is being advanced through the vessel lumen to the desired site of deployment, as well as after deployment. Since it offers high fluoroscopic visibility in a very thin layer, the presence of the gold film allows the thickness of the stent wall to be determined almost solely by considerations of mechanical strength, with consequent reduction of stent external diameter over what would be required if enhanced radiopacity of the base metal were an overriding factor.

The noble metal layer may be ultra-thin and is applied to cover the entire stent—interior as well as exterior surfaces and all edges bounding the internal openings in the wall and the ends thereof if the stent is of the hollow, open-ended tube type, or the entire surface of the wire if the stent is of the wire type. The layer is applied in a way—including a two-layer application—to assure an absolute adherence to the underlying metal of the stent and thereby to prevent even any cracking or defects in the homogeneous nobler metal layer, much less resist peeling or flaking of the layer during insertion, and especially during expansion of the diameter of the stent as it is being deployed in final position in the artery at the target site.

As pointed out in the '045 patent gold is non-irritating and substantially non-allergenic, which allows a gold-plated stent to be implanted even in patients with severe materials allergies. Finally, but by no means of lesser importance, the gold layer offers a surface of substantially non-thrombogenic characteristics, and therefore reduces the likelihood of an acute closure of the vessel in which it is implanted. And if an acute closure is avoided, it is much more likely that the lumen will kept more permanently open in the region occupied by the stent. The surface charge of gold leads to only about 40% or less thrombus formation on a gold-coated stent relative to that encountered with uncoated metal, especially steel, stents.

The disadvantage of reduced mechanical strength of noble metals such as gold or platinum—which makes them unsuitable if sought to be used alone for application in the human vascular system—is overcome by the use of a core composed of a material, such as stainless steel, having considerably better mechanical properties than the noble metal. And the presence of an uninterrupted (i.e., without cracks or related defects), substantially uniform, homogeneous coating of gold or other noble metal has been found by the applicant herein to be of great importance to avoiding a galvanic potential which could ultimately lead to corrosion of the underlying steel or lesser metal. Such a corrosive environment is unacceptable in a stent to be permanently implanted in the body. The highly adherent noble metal coating provides long-term stability and excellent clinical results, and its relatively softer constituency compared to the underlying rigid core of the stent allows at least a slight configurational change upon expansion of the stent to its fully deployed state.

To achieve highly adherent, tight coverage, and a firm and yet lineally extensible bond between the base metal of the stent core or carrier and the noble metal of the outer layer, the '045 patent describes a preferred application of an initial layer of gold by vaporization in a vacuum chamber and then accelerating the gold ions onto and in adherent relationship with the surface of the underlying metal, with stable anchoring thereto, to a thickness of 1 µm or more, followed by a galvanic process to provide a relatively uniform, overall layer thickness of from about 3 to about 6 µm including the initial foundation layer.

The co-pending '053 application describes as a preferred embodiment of its disclosed invention, a stent whose sidewall includes a first solid layer or thickness of a biocompatible base metal, and a second porous layer or thickness which is composed of spherically-shaped metal particles, composed at least in part of a noble metal, which are bonded together to leave spaces between the particles which may serve as a repository for drugs to assist in maintaining the lumen of the vessel open. The second thickness overlies the first thickness in tightly adherent relation thereto, and has a radiopacity which substantially exceeds that of the first thickness, to provide a highly visible view of the stent by x-ray fluoroscopy during its advancement and deployment in the blood vessel, and thereafter whenever the stent is to be examined in place.

A stent embodiment described in the '053 application includes at least one drug selected from a group consisting of anti-thrombotic, anti-platelet, anti-inflammatory and anti-proliferative drugs, residing in the repository. A biodegradable carrier may be used to retain the drugs for timed release thereof from the repository when the stent is deployed at the selected implant site in the blood vessel. Alternatively, the mere spacing of the metal particles may advantageously provide a timed release of the drugs from the repository. Preferably, for that purpose the particles, which are sized in a range of diameters, are located with the larger diameter sizes adjacent and bonded to the surface of the first thickness and with those and progressively smaller diameter sizes bonded together up to the outermost region of the second thickness. In either event, the anti-platelet and/or anti-thrombotic drugs are preferably infused into the porous layer repository, i.e., into the spaces or interstices between the particles, existing at the inward facing surface (and if desired, at directly adjacent edges of the openings) of the stent to inhibit clogging of the lumen as a result of interaction between the stent itself and the blood flow therethrough. Similarly, the anti-inflammatory and/or anti-proliferative drugs are preferably infused into the repository existing at the outward facing surface (and if desired, at directly adjacent edges of the openings) of the stent to inhibit restenosis as a result of fibrosis or proliferation of tissue from trauma to the inner lining of the vessel arising from contact with the stent.

According to the invention described in the '053 application, a third layer or thickness of a ceramic-like material—preferably of either iridium oxide or titanium nitrate—is applied as a coating overlying exposed surfaces of the metal particles in tightly adherent relation to the second thickness at those surfaces, without filling or blocking the spaces between the particles, so that the repository for drugs originally formed in the second thickness remains available. Consequently, the desired drugs may be infused into the spaces between particles, in preferential locations as noted above, for retention and dispensing in the same manner as if the third thickness had not been applied. Additionally, the ceramic-like material is resistant to tissue irritation to further avoid traumatic response during contact of the stent with the inner lining of the vessel at the site.

In a method of fabricating such a multi-layer vascular or endoluminal stent, a porous layer of substantially spherical metal particles is applied atop surfaces of a base metal of the stent, the metal particles at the base metal surfaces being bonded thereto and the metal particles throughout the porous layer being bonded together, with voids therebetween forming a reservoir for retention and dispensing of drugs from the stent when deployed in its vascular or endoluminal location. The metal particles exhibit a radiopacity that substantially exceeds the radiopacity of the base metal for high visibility viewing of the stent by fluoroscopy when advanced and deployed in the body. After applying the porous layer, the exposed surfaces of the metal particles are coated with ceramic-like material consisting of iridium oxide or titanium nitrate while leaving the voids between the particles unblocked and substantially intact so that the reservoir remains available for infusing drugs therein.

The base metal may, for example, be 316L stainless steel, chromium, nickel, titanium, or iridium, or nitinol which is a shape memory nickel-titanium alloy, nominally of 70 µm thickness. The metal particles of platinum-iridium alloy preferably have diameters ranging from about 50 to 500 nanometers (nm), and the porous layer is applied atop the base metal to a thickness in a range from approximately 4 to 8 µm. The iridium oxide or titanium nitrate is coated on surfaces of the metal particles to a thickness in a range from approximately 50 to 500 nm. Thereafter, following steps of rinsing, cleaning and drying, the desired drugs or other selected agents are infused into the reservoir provided by the voids or interstices between particles of the porous layer. Timed release of the drugs may be achieved by incorporating them in a biodegradable carrier.

Gene transfer may alternatively be used to inhibit proliferation of smooth muscle cells, to prevent restenosis that could block the lumen of the vessel in which the stent is deployed. In this technique, a viral vector transfers at least part of the genetic information of interest to the target cell. A gene transfer agent constituting the viral vector or virus is incorporated in a biodegradable carrier, or microspheres or liposomes as the viral vector are contained in solution, and the combination is infused into the reservoir of the multi-layer stent from which it is released in a substantially programmed manner to effect the gene transfer.

The present invention, like the invention of the '053 application, has an underlying concept of providing a stent structure having three fundamental layers, a first underlying layer or thickness of a base metal that functions to provide high mechanical strength, a second intermediate layer that functions to provide high fluoroscopic visibility—preferably a noble metal layer or alloy thereof—, and a top layer of a particularly beneficial biocompatible material—preferably a ceramic-like material such as iridium oxide or titanium nitrate. It is noteworthy that although the preferred embodiment of the invention described in the '053 application utilized a porous intermediate layer, that application also contemplated the use of a completely solid intermediate layer to provide the high visibility property and a highly suitable surface for strong bonding of the final coating which itself offers a surface for attachment of the drug/agent-containing carrier.

The present invention differs principally in mandating the use of a noble metal intermediate layer—which may be elemental or an alloy principally of a noble metal—but which is uninterrupted, highly adherent for tight coverage and substantially uniform overlying the base layer (as with the invention of the '045 patent), and underlying the relatively rough outer layer of ceramic-like material.

The applicant herein has found that such an intermediate layer tends to assure avoidance of a galvanic potential that would lead to corrosion of the lesser, base metal, including such a condition that may obtain with a layer of ceramic-like metal overlying the base metal at points where fissures might exist were it not for the uninterrupted presence of the intermediate noble metal layer. Accordingly, the three layer stent of the present invention fulfills the purpose of excellent mechanical strength, extremely small physical dimensions, increased visibility, long-term stability, and a highly biocompatible surface that enables rapid endothelialization with extremely low occurrence of restenosis.

BRIEF DESCRIPTION OF THE DRAWINGS

The above and still further aims, objects, features, aspects and attendant advantages of the present invention will become apparent from the following detailed description of a preferred embodiment and process of manufacture thereof constituting the best mode presently contemplated of practicing the invention, when taken in conjunction with the accompanying drawings, in which.

DETAILED DESCRIPTION OF A PREFERRED EMBODIMENT AND METHOD

The '045 patent and the '053 application are incorporated in their entirety into this specification by reference. Nevertheless, for the sake of convenience to the reader, certain portions of the '045 patent and '053 application will be repeated in some detail herein.

Figure 1A:
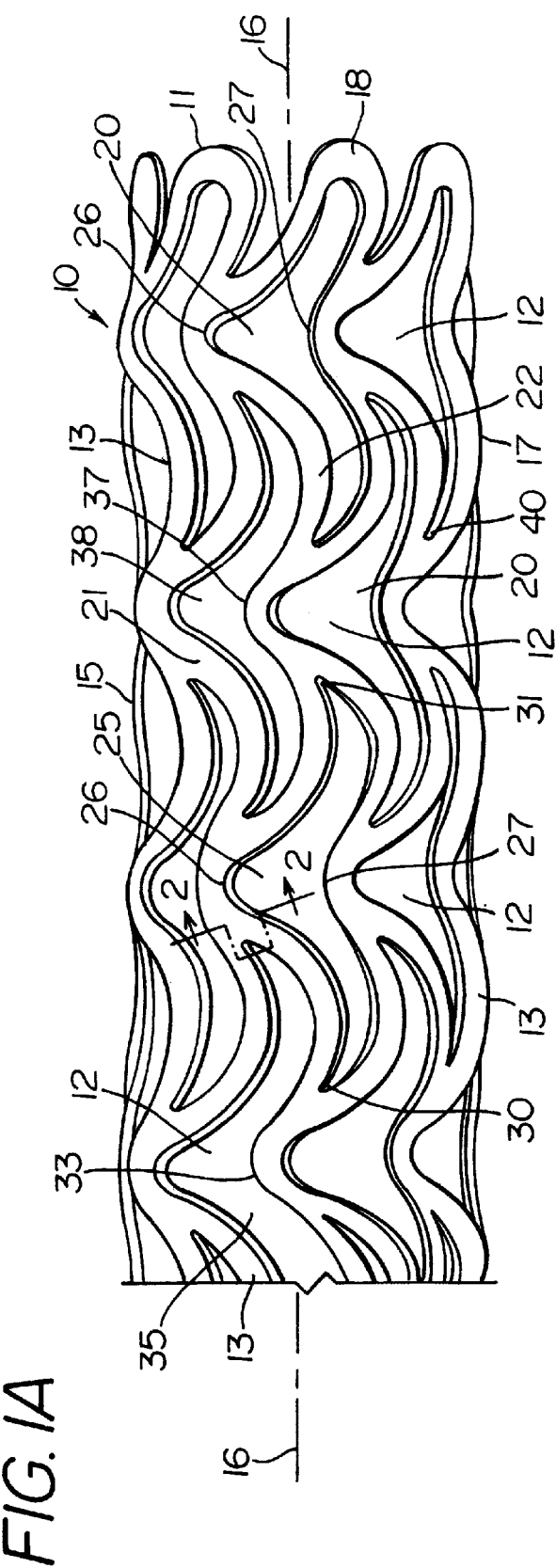
FIGS. 1A and 1B are a fragmentary view, in perspective, of a preferred embodiment of a vascular or endoluminal stent with thin gold plating over its entire surface according to the present invention, and an enlarged detail thereof, respectively.

In FIG. 1A (not to scale) stent 10 is illustrated as being fabricated as a hollow tubular self-supporting structure or member 11 composed of a biocompatible metal such as medical grade 316L stainless steel, although other metals may alternatively be used, such as titanium, iridium, or nitinol, for example. The tubular member is provided with a multiplicity of through-holes or openings 12 through sidewall 15, defined and bounded by a plurality of struts or links 13, which enables expansion of the stent diameter when the device is to be deployed at a target site in a vessel, duct or tract of the human body. The openings 12 may be precisely cut out to form a latticework sidewall using a narrow laser beam of a conventional laser following a programmable pattern. The removed material that formerly occupied openings 12 is discarded following the cutting.

By way of example, the resulting pattern in the latticework sidewall 15 is a network of interconnected struts 13 which are optimized for orientation predominantly parallel to the longitudinal axis 16 of the tube 11, with none of the struts oriented perpendicular (i.e., transverse) to the axis 16, so that no strut interconnecting any other struts in the latticework is oriented to lie completely in a plane transverse to the longitudinal axis, without running from one end of the stent to the opposite end. This type of structure, which is described in detail in applicant's co-pending application Ser. No. 08/933,627, also incorporated by reference in its entirety herein, provides a relatively very low friction characteristic (or coefficient of friction) of the outer surface 17 of the stent, to ease advancement of stent 10 in a vessel, duct or tract to a site for deployment. The network or latticework of struts 13 may define a series of longitudinally repeating circumferential rows 20 of openings 12, in which each opening has a shape which resembles the outline of a handlebar moustache, or of a Dutch winged cap, with each opening bounded by alternating links in wavelets of higher and lower crests in successive rows of each circumferential column displaced along the length of the cylindrical element. If viewed upside down, the openings have a shape resembling the outline of a ram's head with horns projecting at either side upwardly from the head and then downwardly, each opening bounded by alternating links in wavelets of shallower and deeper troughs in successive rows of each circumferential column displaced along the length of the cylindrical element.

Each pair of struts such as 21, 22 bounding an opening 12 in any given row 25 are in the shape of circumferentially displaced wavelets with adjacent circumferentially aligned higher and lower crests 26, 27, respectively, in which the wavelets intersect (30) one another at one or both sides of the crests (30, 31). The intersection 30 of struts (or wavelets) at one side of the adjacent circumferentially aligned crests 26, 27 of row 25 is tangential to a crest 33 of the immediately adjacent row 35, and the intersection 31 of struts (or wavelets) at the other side of those crests is tangential to a crest 37 of the immediately adjacent row 38. Interconnecting points such as 40 between the struts may be notched to enhance symmetrical radial expansion of the stent during deployment thereof.

When the stent 10 is crimped onto a small diameter (low profile) delivery balloon (not shown), the adjacent circumferentially aligned crests of each row move closer together, and these portions will then fit into each other, as the pattern formed by the latticework of struts allows substantial nesting together of the crests and bows, which assures a relatively small circumference of the stent in the crimped condition. Such a stent is highly flexible, and is capable of undergoing bending to a small radius corresponding to radii of particularly tortuous coronary arteries encountered in some individuals, without permanent plastic deformation.

As the stent 10 is partially opened by inflation of the balloon during deployment, the adjacent crests begin to separate and the angle of division between struts begins to open. When the stent is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, to assure a rigid structure which is highly resistant to recoil of the vessel wall following stent deployment. The particular configuration of the stent structure, while highly desirable, is illustrative only and not essential to the principles of the present invention.

The stent may be pre-opened after fabrication to relieve stresses. Pre-opening produces a stent inner diameter that allows the stent to slide comfortably over the uninflated mounting balloon, for ease of crimping the stent onto the balloon. Annealing may be performed after pre-opening by heating the stent structure to an appropriate temperature for a predetermined interval of time.

Figure 1B:
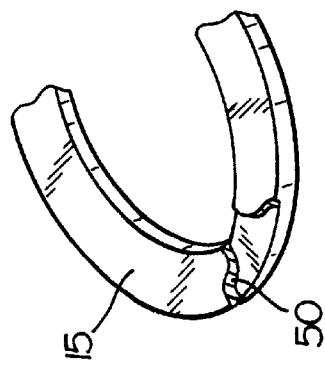

Before or after the pre-opening and annealing steps, the stent is coated with a thin, tightly adherent layer 50 (FIG. 1B, shown partly in section for clarity) of noble metal, preferably gold, but alternatively an alloy which is primarily composed of gold or other noble metal. The noble metal layer is applied to cover the entire exposed surface of the basic metal stent, whether it be of the tubular type as has been described, or a metal mesh, or other configuration. Preferably, the layer has a thickness in the range from approximately 1 μm to approximately 20 μm, and more preferably about five μm.

The thin, adherent film or layer 50 of gold of suitable characteristics may be provided by means of one or more conventional processes, but preferably by a process that commences with ion beam deposition of gold onto the surface of the core or base metal to provide a firm, tightly bonded, extremely thin foundation layer, which allows the bond between base metal and noble metal to flex without suffering fracture or peeling of the overlying layer. Gold ions from vaporized gold are accelerated in a vacuum environment to deposit on the exposed surfaces of the metal core of the stent. Preferably, this initial foundation layer is built upon by then employing a conventional galvanic process to apply one or more additional thin, tightly adherent uniform layers of gold onto the foundation layer or intervening layer as the case may be, to form an overall composite layer of gold having a thickness of from about 3 μm to about 6 μm, and preferably about 5 μm on each side of the wall of the stent. Preferably, at least two layers, one produced by the ion deposition and the other by the galvanic deposition, are applied to the base thickness of the stent wall. For the latter portion of the process, for example, a stainless steel stent may be used as one of a pair of electrodes submerged in an electrolytic bath of appropriate solution of gold constituency and a voltage then applied across the electrodes to establish a current of sufficient magnitude to form a thin electroplate layer of gold on the stent. The overall effect of these processes is to provide the adherence that will preclude cracking, peeling or flaking of any portion of the overall gold layer from the underlying surface of the steel core, which would otherwise tend to occur during times when the stent is undergoing mechanical stress and distortion, such as during the pre-opening, crimping, and expansion-during-deployment phases of the procedure.

To eliminate the presence of impurities that may be attracted to the surface of the gold as a consequence of the overall deposition process or thereafter, the coated stent is preferably subjected to a cleansing step by heating under vacuum to a temperature which will depend upon the nature of the coating and the underlying material. In the case of gold on steel, for example, the cleansing step may be carried out at a temperature of about 250° Celsius and a pressure of about 0.10 atmosphere. It is possible that the annealing step referred to earlier may be carried out as part of the cleansing step where that portion of the process is performed after the gold coating has been applied.

Figure 2:
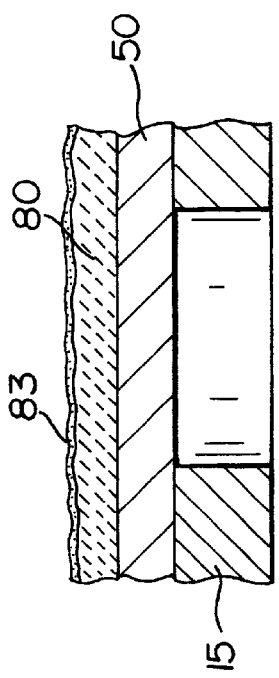
FIG. 2 is a cross-sectional view of the three-layer stent embodiment of the present invention.

A stent 10 fabricated according to the present invention is composed of three different primary or fundamental layers as shown in the greatly exaggerated fragmentary cross-sectional view of FIG. 2, taken through the line 2—2 of FIG. 1A. By "primary" and "fundamental", as used here, it is meant and intended that although the stent may have additional layers, coatings or films, the three layers—two of which have been described thus far—are essential to the favorable characteristics enjoyed by the stent.

The third or upper or outermost or superficial layer 80 is preferably composed of a ceramic-like metal material such as either iridium oxide (IROX) or titanium nitrate, these materials being exemplary of a biocompatible layer that serves a primary purpose of avoiding tissue irritation and thrombus formation. This outermost layer may be deposited as an inert coating over the surface(s) of the underlying intermediate noble metal layer by any known method, preferably to a thickness in the range from about 500 nm to about 1,500 nm (=1.5 μm). This outermost layer is also preferably applied to both sides (and indeed, all exposed surfaces) of the wall of stent 10, so it is the surface that contacts both the inner lining of the vessel and the blood flowing through the lumen of the vessel in which the stent is implanted (deployed).

A high voltage sputtering process is among many suitable processes that may be used to form this outermost coating. Others include anionic oxidation and thermal oxidation. Oxalic acid, application of current and heat, and additional use of an ultrasound bath have been found to produce a very tight adhesion of iridium oxide to the underlying intermediate layer. Suitable processes for forming iridium oxide or titanium nitrate layers also have been developed and can be performed by Hittman Materials & Medical Components, Inc. Of Columbia, Md., for example. If desired, the outermost layer 80 may be formed with a relatively rough surface, so that reservoirs or repositories are present therein for infusion and retention of beneficial drugs.

In addition to assuring the absence of a galvanic potential that could cause corrosion of the base layer, the intermediate noble metal layer serves to enable flexing of the stent over a vast number of cycles encountered in actual use without loss of the overlying iridium oxide or titanium nitrate coating from flaking, shedding or disintegration. Desired anti-inflammatory and/or anti-proliferation drugs may be applied to enter the interstices of the rough outward facing surface and adjacent edges of openings of the stent. The desired anti-thrombotic and/or anti-platelet agents are applied to enter the interstices at the rough inward facing surface and adjacent edges of openings of the stent. By virtue of this repository, the drugs or agents are, to an extent, time released therefrom to provide a primarily acute response to tissue trauma and clotting mechanisms.

Additionally, or alternatively, the timed release of the beneficial drugs from the interstices of the outermost layer 80 may be controlled by incorporating the drugs in a biodegradable carrier, preferably of a type described in the applicant's U.S. patent application Ser. No. 08/798,333, now U.S. Pat. No. 5,788,979. The carrier itself, represented at 83 in the fragmentary exaggerated cross-section of FIG. 2, is formulated to incorporate the drugs or other applicable agents therein. Time-controlled release of the drugs is attributable to the degradation or disintegration of the carrier itself, so that the drug or other agent remains captive within the carrier until it is dispensed or released, i.e., freed from its host, by progressive dissolution upon continuing diffusion of the carrier from the reservoir. The drug tends to act locally rather than systemically in such an arrangement.

As an alternative to the infusion or incorporation of anti-proliferative or anti-inflammatory drugs into the reservoir along the outward facing porous structure of the outer layer, gene transfer may be used to inhibit the smooth muscle cell growth that leads to neointima and restenosis. In principle, a viral vector is used to transfer the desired information into the genome of the target cells. Viruses capable of such gene transfer are, for example, adenovirus and herpervirus, or fractions of the virus. By viral transfer, which is believed to occur by virtue of absorption and diffusion, part of the genetic information of interest is provided to the target cell. Such information can relate to several mechanisms of smooth muscle cell proliferation, with the aim of inhibiting restenosis which, if unchecked, could result in at least partial and perhaps complete blockage of the vessel's lumen, despite the presence of the deployed stent at the site.

One important technique involves blocking the proliferation stimulating factors such as cytoKines, n Fkappa b, platelet derived growth factors or other growth factors that originate from platelet deposition, thrombus formation, mechanical stress, or injury and inflammation. The applicant herein is currently investigating whether selective inducement of apoptosis—or programmed cell death—may be achieved via the fas-ligand, which would enable a programmed intervention against overshooting cellular proliferation in a narrowly controlled region of the tissue.

The virus transfer is performed by incorporating the gene transfer agent—a viral vector or virus of the above-mentioned type that contains the viral genetic information desired to be transferred to the target cell(s)—into a biodegradable carrier for release from the reservoir into which it has been infused and dispensed by the process of biodegradation. Alternatively, the release to effect the gene transfer may be accomplished by release from a solution in the reservoir which contains liposomes as the viral vector.

The final or outermost layer is, in any event, formed with a sufficiently rough exposed surface to assure some attachment of a carrier incorporating the aforementioned drugs or other agents therein.

The three layer structure can be produced with an overall thickness of less than 50 $\mu$m. The stainless steel core may be fabricated in a thickness of approximately 35 $\mu$m, which offers sufficient mechanical strength to resist the natural recoil of the blood vessel wall following deployment of the stent. The noble metal, preferably gold intermediate layer is applied in a preferably 5 $\mu$m thickness to all exposed surfaces of the base layer, giving a total additional thickness of 10 $\mu$m to the structure, and serving to avoid a galvanic potential. The outermost IROX layer or oxide, hydroxide or nitrate of a noble metal applied to a thickness of up to about 1.5 $\mu$m atop the intermediate layer provides a highly biocompatible surface for the overall stent. The capability to provide a stent structure with such features and advantages in a physical thickness of 50 $\mu$m or less is an important aspect of the present invention.

Although certain preferred embodiments and methods have been disclosed herein, it will be appreciated by those skilled in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A vascular or endoluminal stent adapted to be implanted in a selected vessel, duct or tract of a human body to maintain an open lumen at the site of the implant, comprising a biocompatible metal hollow tube having a multiplicity of openings through an open-ended tubular sidewall thereof as a base layer which is biologically compatible with the blood and tissue of the human body, said tube constituting a single member from which the entire stent is fabricated; a thin, tightly adherent intermediate layer of a noble metal of substantially greater radiopacity than the base layer overlying the entire exposed surface area of said tube including edges of said openings as well as exterior and interior surfaces and ends of said sidewall; and a highly biocompatible ceramic-like metal outermost layer adherent to and overlying said intermediate layer.

2. The stent of claim 1, wherein the overall thickness of the sidewall is less than or equal to 50 $\mu$m.

3. The stent of claim 1, wherein the outermost layer has a rough outer surface for retention of drugs to be time released therefrom after the stent is implanted, to assist the stent in maintaining said lumen open.

4. The stent of claim 3, wherein said outermost layer is composed of iridium oxide.

5. The stent of claim 3, wherein the sidewall has an outward facing surface, an inward facing surface, and edges along holes through the sidewall and the open ends thereof, and said drug-retention outer surface is present along at least one of said outward facing surface and said inward facing surface.

6. The stent of claim 3, wherein said outermost layer has a thickness in a range from about 500 nm to about 1500 nm.

7. The stent of claim 1, wherein said intermediate layer is composed of gold with a substantially uniform thickness in a range from about 3 to about 6 $\mu$m.

8. The stent of claim 1, wherein at least one drug selected from a group consisting of anti-thrombotic, anti-platelet, anti-inflammatory and anti-proliferative drugs is present on said outermost layer.

9. The stent of claim 8, wherein said at least one drug is incorporated in a biodegradable material for timed release of the drug.

10. The stent of claim 1, wherein a viral vector is present on said outermost layer and selected for transfer of genetic information to target cells in tissue at the inner lining of said vessel, duct or tract to inhibit proliferation of tissue growth thereat.

11. The stent of claim 10, wherein said viral vector is incorporated in a biodegradable material.

12. The stent of claim 5, wherein an anti-thrombotic drug is present on said inward facing surface, and an anti-inflammatory drug is present on said outward facing surface.

13. The stent of claim 12, wherein said drugs are incorporated in a biodegradable material for timed release thereof from the rough outer surface when said stent is implanted.

14. The stent of claim 1, wherein said ceramic-like material is selected from a group consisting of iridium oxide or titanium nitrate.

15. The stent of claim 1, wherein said base layer is medical grade stainless steel.

16. A metallic device acceptable for implantation in a human body, comprising a biocompatible metal base; a thin, continuous, tightly adherent first layer of noble metal or alloy thereof overlying an exposed surface area of said metal base; and a biocompatible metal outer layer having a relatively rough porous surface with interstices therein adherent to and overlying said first layer.

17. The device of claim 16, wherein said base is hollow and the composite thickness of said base, said first layer and said outer layer is less than approximately 60 $\mu$m.

18. The device of claim 16, wherein the interstices in said rough porous surface of said outer layer are at least partially filled with a substance selected to enhance the compatibility of the device in the body in which it is to be implanted.

19. The device of claim 18, wherein said substance is contained within a carrier which is biodegradable in the presence of body fluid, for release of said substance from the carrier during disintegration thereof.

20. The device of claim 16, wherein said first layer and said outer layer are selected to avoid a substantial galvanic potential therebetween.

21. The device of claim 20, wherein said first layer is at least primarily composed of gold and said outer layer is selected from a group consisting of an oxide, hydroxide or nitrate of a metal compatible with said first layer.

22. The device of claim 21, wherein said compatible metal is a noble metal.

23. The device of claim 21, wherein said first layer has a thickness in a range from approximately 3 µm to approximately 6 µm, and said outer layer has a thickness in a range from approximately 500 nm to approximately 1.5 µm.

24. The device of claim 17, wherein said first layer is at least primarily composed of gold and said outer layer is selected from a group consisting of an oxide, hydroxide or nitrate of a metal compatible with said first layer.

25. The device of claim 24, wherein said compatible metal is a noble metal.

26. The device of claim 24, wherein said first layer has a thickness in a range from about 3 µm to about 6 µm covering both sides of the hollow base, and said outer layer has a thickness in a range from about 500 nm to about 1.5 µm.

27. The device of claim 26, wherein said device is a stent for implantation in a blood vessel of the body or in an endoluminal duct or tract of the body for maintaining an open lumen at the implant site of the stent, and said hollow base has a thickness sufficient to resist recoil of the vessel, duct or tract after expansion of the stent to its fully deployed diameter therein.

28. The device of claim 27, wherein said base is composed of stainless steel having a thickness equal to or less than about 50 µm.

29. The device of claim 27, wherein the interstices in said rough porous surface of said outer layer at both sides of said base of the stent are at least partially filled with drugs selected to inhibit closure of the central lumen of said stent and to inhibit inflammation and proliferation of tissue in the vessel, duct or tract at the implant site of the stent therein.

30. The device of claim 29, wherein said at least partial fill of drugs is of adequate amount to reduce friction for facilitating advancement of the stent through the vessel, duct or tract to said implant site.

31. The device of claim 29, wherein said drugs are contained within a carrier which is biodegradable in the presence of body fluid, for release of said drugs from the carrier during disintegration thereof.

32. The device of claim 27, wherein said rough porous surface of said outer layer at both sides of said base of the stent has a vector present thereon selected for transfer of genetic information to target cells in tissue at the inner lining of said vessel, duct or tract to inhibit proliferation of tissue growth at the implant site of the stent.

33. The device of claim 32, wherein said vector is incorporated in a biodegradable carrier on said rough porous surface.

34. The device of claim 32, wherein said vector is a viral vector.

35. The device of claim 32, wherein said vector is a non-viral vector.

36. The device of claim 23, wherein said rough porous surface of said outer layer at both sides of said base has a vector present thereon selected for transfer of genetic information to target cells in tissue at the implant site of the device.

37. The device of claim 36, wherein said vector is incorporated in a biodegradable carrier on said rough porous surface.

38. A device adapted to be implanted in a human body, comprising a substantially continuous inner layer of noble metal or alloy; and a biocompatible outer layer of an oxide, hydroxide or nitrate of metal having a comparatively rough porous surface and a galvanic potential relative to said inner layer which is insufficient to cause deterioration of metal in contact with said inner layer; said outer layer overlying and in intimate bonded relation to said inner layer.

39. The device of claim 38, wherein said outer layer is composed of iridium oxide.

40. The device of claim 39, including a stainless steel base underlying and adhered to said inner layer remote from said outer layer.

41. The device of claim 40, wherein said device is a stent, said base is a tube having a sidewall laced with struts separated by holes through the sidewall, said struts having a composite thickness less than about 60 µm which includes the thicknesses of said overlying inner and outer layers.

* * * * *